United States Patent
Kampman et al.

(10) Patent No.: US 9,017,265 B2
(45) Date of Patent: Apr. 28, 2015

(54) TRANSFER OF MEASUREMENT DATA RELATED TO PHYSICAL EXERCISE

(71) Applicant: Polar Electro Oy, Kempele (FI)

(72) Inventors: Ville Kampman, Oulu (FI); Tuomas Jomppanen, Oulu (FI)

(73) Assignee: Polar Electro Oy, Kempele (FI)

( * ) Notice: Subject to any disclaimer, the term of this patent is extended or adjusted under 35 U.S.C. 154(b) by 0 days.

(21) Appl. No.: 13/957,956

(22) Filed: Aug. 2, 2013

(65) Prior Publication Data

US 2014/0039329 A1 Feb. 6, 2014

Related U.S. Application Data

(60) Provisional application No. 61/679,145, filed on Aug. 3, 2012.

(30) Foreign Application Priority Data

Aug. 3, 2012 (GB) .................................. 1213823.6
Nov. 8, 2012 (GB) .................................. 1220154.7

(51) Int. Cl.
*A61B 5/0255* (2006.01)
*A61B 5/00* (2006.01)
*A61B 5/024* (2006.01)

(52) U.S. Cl.
CPC ............. *A61B 5/7278* (2013.01); *A61B 5/024* (2013.01); *A61B 5/0004* (2013.01);
(Continued)

(58) Field of Classification Search
CPC .................................................. A63B 24/0062
USPC ....................................................... 600/508
See application file for complete search history.

(56) References Cited

U.S. PATENT DOCUMENTS 6,601,016 B1 * 7/2003 Brown et al. ............... 702/182
7,914,418 B2 * 3/2011 Nissila ........................ 482/4
(Continued)

FOREIGN PATENT DOCUMENTS

EP 0922434 6/1999
EP 0922434 A1 6/1999
(Continued)

OTHER PUBLICATIONS

Combined Search and Examination Report for application No. GB1220154.7 dated Dec. 6, 2012.
(Continued)

*Primary Examiner* — Michael Kahelin
(74) *Attorney, Agent, or Firm* — Hoffmann & Baron, LLP

(57) ABSTRACT

A system for processing heart rate measurement data includes a server computer configured to: associate, during a registration procedure for a measurement device of a user, a device identifier of the measurement device with a user account of the user stored in the server computer; receive a device identifier and real-time heart rate measurement data over a network connection; identify the user's measurement device from the received device identifier; store the received heart rate measurement data to the user account of the user on the basis of the association between the received device identifier and the corresponding user account; compute, repeatedly during the physical exercise from the received heart rate measurement data, advanced performance data comprising at least one value which accumulates during the physical exercise; and transmit the computed advanced performance data to the equipment interface unit over the network connection during the physical exercise.

8 Claims, 3 Drawing Sheets

(52) U.S. Cl.
CPC ............ *A61B 5/4848* (2013.01); *A61B 5/4866* (2013.01); *A61B 5/4875* (2013.01); *A61B 5/7475* (2013.01); *A61B 5/0022* (2013.01); *A61B 5/0006* (2013.01); *A61B 5/002* (2013.01); *A61B 2505/09* (2013.01)

(56) References Cited

U.S. PATENT DOCUMENTS

| | | | |
|---|---|---|---|
| 2002/0042328 | A1 | 4/2002 | Yoo |
| 2005/0070809 | A1 | 3/2005 | Acres |
| 2005/0166239 | A1* | 7/2005 | Uchikubo et al. ............. 725/78 |
| 2007/0219059 | A1 | 9/2007 | Schwartz et al. |
| 2008/0281165 | A1* | 11/2008 | Rai et al. ....................... 600/300 |
| 2011/0165998 | A1 | 7/2011 | Lau et al. |

FOREIGN PATENT DOCUMENTS

| | | |
|---|---|---|
| EP | 2025370 | 2/2009 |
| EP | 2108311 | 10/2009 |
| EP | 2108311 A1 | 10/2009 |
| EP | 2260910 | 12/2010 |
| EP | 2260910 A1 | 12/2010 |
| WO | 0187426 | 11/2001 |
| WO | WO0187426 A2 | 11/2001 |
| WO | 2008046443 | 4/2008 |
| WO | 2008071843 | 6/2008 |
| WO | WO2008071843 A1 | 6/2008 |

OTHER PUBLICATIONS

Combined Search and Examination Report for application No. GB1213823.6 dated Sep. 24, 2012.
International Search Report for PCT/FI2013/050769 dated Oct. 24, 2013.
Office Action for corresponding Application No. GB1220154.7, dated May 24, 2013, 2 pages.
Office Action for corresponding Application No. GB1220154.7, dated Apr. 24, 2013, 3 pages.
Office Action for corresponding Application No. GB1220154.7, dated Feb. 26, 2013, 3 pages.
Office Action for corresponding Application No. GB1213823.6, dated Sep. 24, 2012, 7 pages.
Office Action for corresponding Application No. GB1220154.7, dated Dec. 6, 2012, 9 pages.

* cited by examiner

TRANSFER OF MEASUREMENT DATA RELATED TO PHYSICAL EXERCISE

CROSS-REFERENCE TO RELATED APPLICATIONS'

This application claims priority based on Great Britain Patent Application No. 1213823.6, filed Aug. 3, 2012, U.S. Provisional Patent Application No. 61/679,145, filed Aug. 3, 2012, and Great Britain Patent Application No. 1220154.7, filed Nov. 8, 2012, which are incorporated herein by reference in their entirety.

BACKGROUND

1. Field

The invention relates to the field of physical exercise devices and, particularly, to transfer of exercise data to a network storage.

2. Description of the Related Art

Modern physical exercise devices typically comprise measurement units comprising sensors attachable to a user's body and user interface devices. A measurement unit measures exercise data from the user's body and transmit to a user interface unit for display to the user during an exercise. The user interface unit may also comprise an input/output interface to store the measured exercise data to a network storage, e.g. a computer or a server, after the exercise.

SUMMARY

According to an aspect, there is provided a system for processing heart rate measurement data measured during a physical exercise of a user, the system comprising a server computer comprising at least one processor and at least one memory including a computer program code, wherein the at least one memory and the computer program code are configured, with the at least one processor, to cause the server computer to: store a plurality of user accounts; associate, during a registration procedure for a measurement device of a user, a device address of the measurement device with a user account of the user stored in the server computer, wherein the measurement device is arranged to provide heart rate measurement data, and wherein the device address comprises a medium access control address or an internet protocol address of the measurement device; receive, from an equipment interface unit, a device address and real-time heart rate measurement data over a network connection, wherein the received device address comprises a medium access control address or an internet protocol address; store the received heart rate measurement data to the user account of the user on the basis of the association between the received device address and the corresponding user account; compute, repeatedly during the physical exercise from the received heart rate measurement data, advanced performance data of the user comprising at least one value which accumulates during the physical exercise; transmit the computed advanced performance data to the equipment interface unit over the network connection during the physical exercise so as to output the advanced performance data to the user.

According to another aspect, there is provided an apparatus comprising: a wireless interface configured to provide a wireless device-to-device connection with a measurement device; a network interface configured to provide the apparatus with a network connection; a user interface; at least one processor; and at least one memory including a computer program code, wherein the at least one memory and the computer program code are configured, with the at least one processor, to cause the apparatus to: receive, at a beginning of an exercise carried out by a user, a device address from a measurement device attachable to the user's body, wherein the device address comprises a medium access control address or an internet protocol address of the measurement device; determine a network address of a server computer to which to route real-time heart rate measurement data acquired from the measurement device during the exercise; receive said heart rate measurement data from the measurement device through the wireless interface during the exercise; and cause the network interface to transmit the device address and the heart rate measurement data through the network connection to the network address of the server computer, wherein the server computer uses the device address to store the heart rate measurement data to a correct user account, and wherein the server computer computes, repeatedly during the physical exercise from the heart rate measurement data it receives, advanced performance data comprising at least one value which accumulates during the physical exercise; receive the advanced performance data from the server computer over the network connection during the physical exercise; and output the advanced performance data to the user.

According to another aspect, there is provided a method for processing heart rate measurement data measured during a physical exercise of a user, the method comprising: storing, in a server computer, a plurality of user accounts; associating, in the server computer during a registration procedure for a measurement device of a user, a device address of the measurement device with a user account of the user stored in the server computer, wherein the device address comprises a medium access control address or an internet protocol address of the measurement device; receiving, in the server computer, a device address and real-time heart rate measurement data from an equipment interface unit over a network connection, wherein the device address comprises a medium access control address or an internet protocol address; storing, in the server computer, the received heart rate measurement data to the user account of the user on the basis of the association between the received device address and the corresponding user account; computing, in the server computer repeatedly during the physical exercise from the received heart rate measurement data, advanced performance data comprising at least one value which accumulates during the physical exercise; transmitting the computed advanced performance data from the server computer to the equipment interface unit over the network connection during the physical exercise so as to output the advanced performance data to the user.

Embodiments of the invention are defined in the dependent claims.

BRIEF DESCRIPTION OF THE DRAWINGS

Embodiments of the present invention are described below, by way of example only, with reference to the accompanying drawings, in which.

DETAILED DESCRIPTION

The following embodiments are exemplary. Although the specification may refer to "an", "one", or "some" embodiment(s) in several locations, this does not necessarily mean that each such reference is to the same embodiment(s), or that the feature only applies to a single embodiment. Single features of different embodiments may also be combined to provide other embodiments. Furthermore, words "comprising" and "including" should be understood as not limiting the described embodiments to consist of only those features that have been mentioned and such embodiments may contain also features/structures that have not been specifically mentioned.

Figure 1:
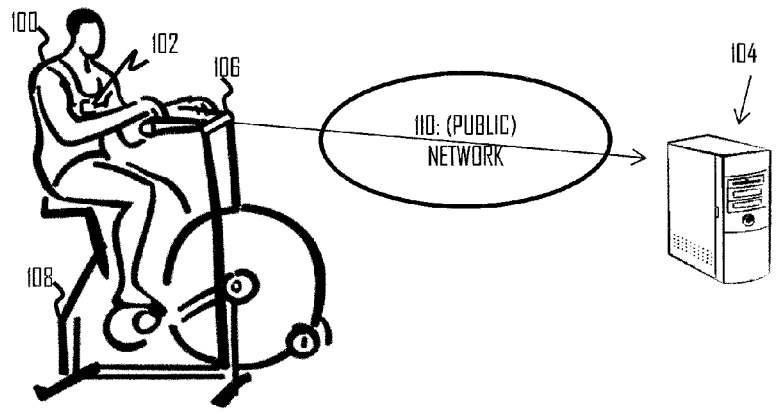
FIG. 1 illustrates a performance monitoring arrangement according to an embodiment of the invention.

FIG. 1 illustrates a performance monitoring arrangement according to an embodiment of the invention. Referring to FIG. 1, a user 100 carries out a physical exercise in a gym or in a similar training environment by using a training device 108, e.g. a treadmill, an exercise cycle, or a rowing machine. A measurement device 102 is attached to the user's 100 body to measure physiological data during the exercise. The measurement device 102 may be a heart rate sensor comprising at least one sensor to measure a heart rate of the user 100. The measurement device 102 may transmit measured heart rate measurement data wirelessly to an equipment interface unit 106. A wireless transmission may utilize one of the following short range device-to-device communication technologies: Bluetooth, Bluetooth Low Energy, Polar-compatible magnetic pulse operating on 5 kHz radio band, ANT by Dynastream, or IEEE 802.15.4. Other short-range device-to-device or network communication protocols are equally possible. The short range device-to-device connection may also be called a proximity connection because of its short communication range. The communication range may be in the order of a couple of meters, e.g. less than five meters.

The equipment interface unit 106 may comprise a user interface to display the received hear rate measurement data to the user 100. In some examples, the equipment interface unit 106 may be worn by the user 100, e.g. a wrist device, but according to an embodiment the equipment interface unit 106 is fixed or attached to the training device 108. When the user 100 approaches and starts to use the training device 108, the connection between the measurement device 102 and the equipment interface unit 106 may be established automatically, e.g. on the basis of the close proximity detection between the devices 102, 106. In addition to displaying or otherwise outputting the received measurement data, the equipment interface unit 106 may be configured to stream the measurement data to a server computer 104. In some cases, the equipment interface unit 106 cannot establish a direct circuit connection with the server computer so the connection may be routed through one or more communication networks 110. At least some of the networks 110 may be public networks, e.g. the Internet. As a consequence, the equipment interface unit 106 may be considered as a network node configured to stream the heart rate measurement data to the server computer 104 during the physical exercise.

Figure 2:
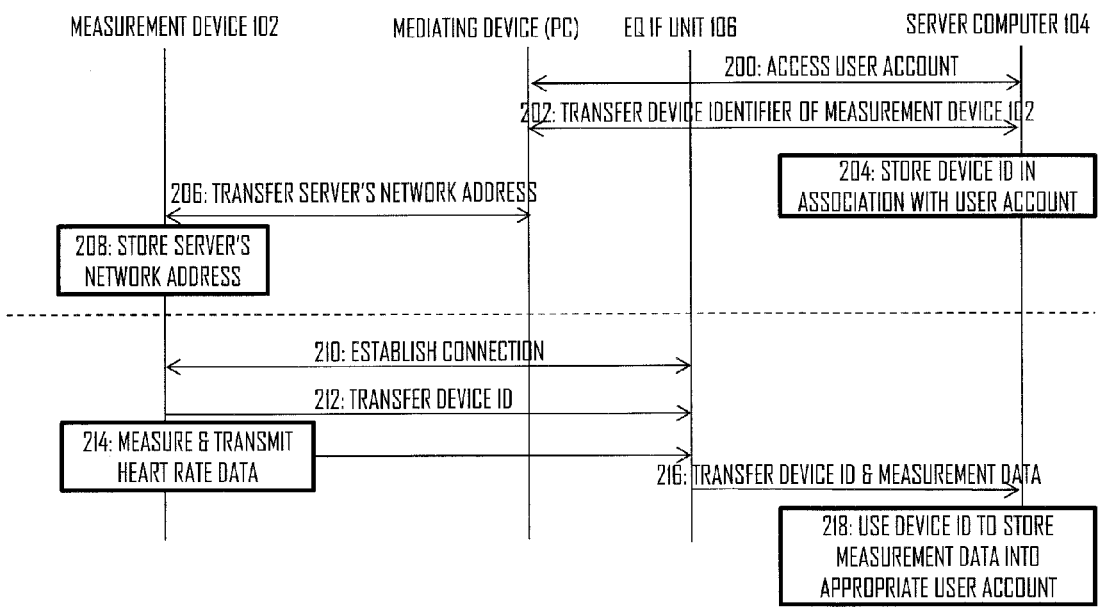
FIG. 2 illustrates a signalling diagram related to the operation of the performance monitoring arrangement according to an embodiment of the invention.

FIG. 2 illustrates a procedure for streaming the heart rate measurement data from the measurement device 102 to the server computer 104 according to an embodiment of the invention. The procedure comprises steps carried out in the measurement device 102, steps carried out in the equipment interface unit 106, steps carried out in the server computer 104, and steps carried out in a mediating device used by the user 100 to connect to the server computer 104 and to manage a user account stored in the server computer 104. The mediating device may be a personal computer (PC), but it should be appreciated that the server computer 104 may be connected by using any device having an internet connection, a web browser, and a connection enabling communication with the measurement device, e.g. a tablet computer, a palm computer, a mobile phone, and a gaming console.

The user account may store physiological data of the user 100 and user attributes such as name, gender, age, weight, height, fitness level, training history comprising measurement data and accumulated performance data, training schedule, maximum oxygen intake (VO2Max), maximum heart rate (HRMax), performance zones (heart rate zones, speed zones), aerobic and anaerobic thresholds. The data stored in the user account may be classified into personal physiological data and personal training data. The personal physiological data may comprise at least some of the gender, age, weight, height, fitness level, maximum oxygen intake (VO2Max), maximum heart rate (HRMax), performance zones (heart rate zones, speed zones), and aerobic and anaerobic thresholds. The personal training data may comprise at least some of the training history comprising measurement data and accumulated performance data, and training schedule. Referring to FIG. 2, let us now describe the operation of the procedure. Before the exercise, e.g. upon buying the measurement device 102, the measurement device 102 may be registered to the server computer 104 by using the mediating device. In step 200, the user 100 accesses his/her user account stored in the server computer 104 by logging into the user account. The user login may follow the principles of a conventional web-based authentication, wherein the user inputs a user name and a password into appropriate fields provided in a web page related to the user accounts stored in the server computer 104. The step 200 may comprise operations in the mediating device such as accessing an URL (Uniform Resource Locator) of the server computer and communicating the user credentials to the server computer 104. The step 200 may also comprise operations in the server computer, e.g. transmitting the web page to the mediating device, receiving the user credentials, and authenticating the credentials.

When the server computer 104 has granted the user 100 access to his/her user account, a device identifier of the measurement device 102 may be transferred to the server computer 104 (step 202), and the server computer 104 may be configured to associate the device identifier of the measurement device 102 with the user's 100 user account (step 204). This may be carried out by storing the device identifier into the user account. Step 202 may be an automatized procedure such that the mediating device may automatically upload the device identifier to the server computer 104 upon being connected to the measurement device and after the user 100 has accessed the user account. As a consequence, no user input is necessary. In another embodiment, the user 100 inputs the device identifier manually into his/her user account.

In an embodiment, the device identifier is a device address of the measurement device, e.g. a medium access control (MAC) address. In another embodiment, the device identifier is an internet protocol address of the measurement device 102. In yet another embodiment, the device identifier is a processor identification code of the measurement device 102.

In step 206, the mediating device transfers the server computer's 104 network address to the measurement device 102, and the measurement device 102 stores the server's network address in step 208. The network address may comprise the URL and/or an internet protocol (IP) address of the server computer 104, for example. It should be appreciated that steps 206 and 208 are optional, and in some embodiments described below these steps are omitted.

Steps 200 to 208 may be carried out during a registration phase related to the setup of the measurement device 102 and/or the configuration of the user account. The registration phase may precede a physical exercise carried out by the user 100 using the measurement device. Let us now consider the operation of the system during the exercise of the user 100 wearing the measurement device 102. At the beginning of the physical exercise with the training device 108, the measurement device 102 pairs with the equipment interface unit 106. The pairing may comprise establishment of the device-to-device communication connection between the devices 102, 106 (step 210). In connection with the pairing, e.g. during the pairing, the measurement device 102 may transmit its device identifier to the equipment interface unit 106 (Step 212).

In an embodiment, the measurement device 102 transmits also the network address of the server computer 104 to the equipment interface unit 106 in step 202. In another embodiment, the equipment interface unit 106 derives the server computer's 104 network address from the device identifier of the measurement device on the basis of a database providing a mapping between device identifiers of measurement devices and associated server computers. For example, the user 100 may have registered his/her measurement device 102 to a database of the gym, and the equipment interface unit 106 may compare the device identifier received in step 212 with device identifiers comprised in the database. Upon discovering the device identifier from the database, the equipment interface unit may determine a server computer associated with that device identifier and retrieve the network address of the associated server computer. In another embodiment, a part of the device identifier identifies the appropriate server computer. For example, all measurement devices having an identical part of the device identifier are associated with the same server computer. The identical part may comprise a determined number of first and/or last digits of the device identifier. The database may store the mapping between the device identifier parts and associated server computers, and the equipment interface unit 106 may be configured to determine the part of the received device identifier that is used to derive the associated server computer, to search the database for a corresponding part of the device identifier, and to retrieve the network address of a server computer associated with the part of the device identifier. The database may be stored in a local network of the equipment interface unit 106 or in a remote network accessible through at least one public network 110. In yet another embodiment, the device identifier is any identifier derived from a unique identifier of the measurement device 102 according to a determined algorithm. For example, the device identifier may be a code computed from the device address of the measurement device 102 according to a determined logic. As a consequence, the device identifier may be an intermediate identifier sequence computed from the device address of a corresponding real identifier received from the measurement device.

As a result, the equipment interface unit 106 acquires a network address of the server computer 104 to which transmit any measurement data received during the exercise. The equipment interface unit may already initiate a network connection with the server computer 104 and to map internally a device-to-device wireless connection with the measurement device 102 to the network connection with the server computer 104.

In step 214, the measurement device measures heart rate measurement data by using at least one of its sensors, processes the measurement data, and transmits the measurement data over the wireless device-to-device connection to the equipment interface unit 106. This procedure may be continuous and continue for the duration of the exercise. The measurement device 102 may transmit the heart rate measurement data constantly as it is measured. The actual transmissions may be intermittent, depending on the wireless communication protocol being used. The heart rate measurement data may be primitive measurement data, e.g. instantaneous heart rate values, average heart rate values averaged over a determined number of heart beats, RR intervals acquired from peak intervals of heart rate signals.

In step 216, the equipment interface unit 216 receives the heart rate measurement data, decodes the received heart rate measurement data, and prepares a message comprising the heart rate measurement data and the device identifier of the measurement device 102. Then, the equipment interface unit 106 may transmit the heart rate measurement data and the device identifier of the measurement device to the server computer 104 over the network connection. In another embodiment, the device identifier may be provided to the server computer 104 during the establishment of the network connection between the equipment interface unit 106 and the server computer 104.

Upon receiving the heart rate measurement data together with the device identifier of the measurement device 102, the server computer may determine a user account to which store the received heart rate measurement data on the basis of the device identifier. As the device identifier has already been associated with a specific user account, the server computer 104 may use the device identifier as the link between the user account and the heart rate measurement data. In step 218, the server computer searches for a user account having the same device identifier as the device identifier associated with the heart rate measurement data received in step 216. Upon discovering the appropriate user account, the server computer stores the received heart rate measurement data to the correct user account in step 218.

The above-described embodiment solves a problem of enabling the equipment interface unit 106 to determine a correct server storing the user account of the user 100. It also solves a problem of enabling the server to store the heart rate measurement received from the equipment interface unit 106 into a correct user account. It should be noted that the equipment interface unit 106 may be used by different users at different times.

According to another point of view, the server computer 104 associates the device identifier of the measurement device 102 with the physiological data and/or user attributes comprised in the user account. The server computer 104 may use this association to process the received measurement data. For example, the server computer 104 may compute energy expenditure from the received heart rate measurement data by using age, weight, and/or gender associated with the measurement device 102 providing the heart rate measurement data.

Figure 3:
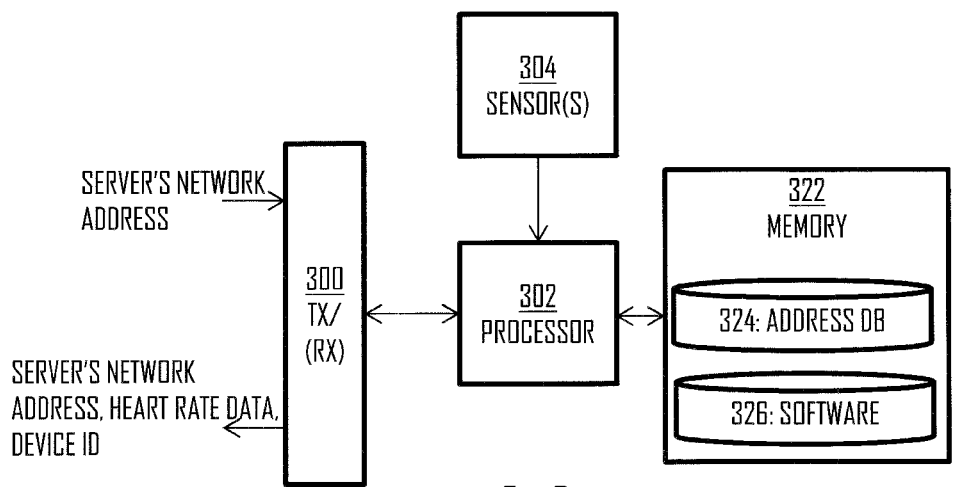
FIG. 3 illustrates a block diagram of a measurement device according to an embodiment of the invention.

Let us now describe embodiments of the structural and functional elements comprised in the measurement device 102, equipment interface unit 106, and the server computer 104 according to some embodiments of the invention with reference to FIGS. 3 to 6. FIG. 3 illustrates a block diagram of the measurement device 102 according to an embodiment of the invention. The measurement device may be a device with no user interface.

Referring to FIG. 3, the measurement device 102 comprises an input/output (I/O) circuitry 300 configured to provide the measurement device 102 with communication capability with other device, e.g. the mediating device and/or the equipment interface unit 106. In an embodiment, the I/O circuitry 300 comprises a wireless communication circuitry configured to operate according to one of the wireless communication protocols listed above, for example. The wireless communication circuitry may be used to transmit at least the device identifier and the measured heart rate measurement data to the equipment interface unit 106 over the wireless connection. In some embodiments, the wireless communication circuitry may be used to receive data and/or operating parameters, e.g. the server's network address. In other embodiments, the server's network address may be received over a wired link established between the measurement device 102 and the mediating device, e.g. a universal serial bus (USB) connection. In yet another embodiment, the I/O circuitry 300 has no reception capability. The I/O circuitry 300 may be considered as a communication circuitry handling the transmission and, in some embodiments, reception of information.

The measurement device 102 further comprises at least one sensor 304 The sensor 304 may be a heart rate sensor configured to measure the user's 100 heart rate. The heart rate sensor may measure the heart rate electrically direct from the user's skin, or it may be an optical heart rate sensor having an optical sensor directed towards the user's 100 skin. The measurement device 102 may further comprise other sensors, e.g. a motion sensor and/or a stride sensor. The sensor(s) 304 may output raw measurement signals comprising electrical and/or optical heart rate signals to a processor 302 configured to process the received raw measurement signals into the heart rate measurement data. The processor 302 may be configured to carry out signal detection for the received raw measurement signals. With respect to the heart rate signals, the processor 302 may be configured to detect a determined waveform in the received heart rate signals and to output a signal to the I/O circuitry 300 upon detecting the determined waveform. The I/O circuitry 300 may then transmit a wireless signal in response to the input from the processor, and wireless signals transmitted by the I/O circuitry represent the detected heart rate measurement data. Depending on the embodiment, the processor 302 may configure the I/O circuitry 300 to transmit the heart rate measurement data as numeric values, or the processor 302 may configure the I/O circuitry 300 to transmit the wireless signal with the same rate as the processor 302 detects the determined waveform in the raw measurement data.

During the establishment of the wireless connection with the equipment interface unit 106, the I/O circuitry 300 may be configured to transmit the device identifier of the measurement device 102 to the equipment interface unit 106. In the embodiments where the measurement device 102 receives the server computer's 104 network address during the registration phase and stores the network address into an address database 324 stored in a memory 322 of the measurement device 102, the I/O circuitry 300 may be configured to retrieve the network address from the address database 324 and transmit the network address to the equipment interface unit 106 during the connection establishment. In such embodiments, the user credentials may also be stored in the address database 324, and the I/O circuitry 300 may be configured to transmit the user credentials to the equipment interface unit 106 so that the equipment interface unit 106 may log into the user's 100 user account for the input of the heart rate measurement data.

The memory 320 may further store a computer program code 326 configuring the operation of the processor 302 and, in some embodiments, at least partly the I/O circuitry 300.

Figure 4:
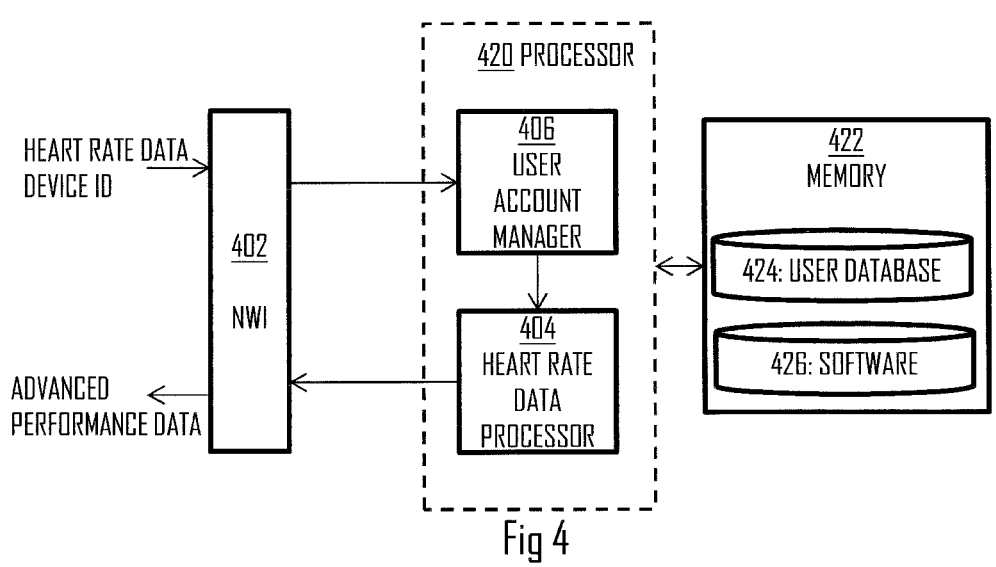
FIG. 4 illustrates a block diagram of a server computer according to an embodiment of the invention.

FIG. 4 illustrates a block diagram of the server computer 104 according to an embodiment of the invention. Referring to FIG. 4, the server computer 104 comprises a network interface 402 providing the server computer with a network connection. The network interface 402 may comprise a network adapter providing a connection to the Internet. The server computer 104 further comprises a processor 420 comprising a user account manager circuitry 406. During the registration phase, the user account manager circuitry 406 may receive the device identifier of the measurement device and store the device identifier in the user's 100 user account in a user account database 424 stored in a memory unit 422 of the server computer 104. During the exercise, the user account manager circuitry 406 may receive the device identifier of the measurement device 102 from the equipment interface unit 106 over the network connection and, in some embodiments, the user credentials authenticating the equipment user interface unit 106 to access the user database. Thereafter, the user account manager circuitry 406 may store any measurement data received from the equipment interface unit 106 to the correct user account associated with the received device identifier. In some embodiments, the user account manager circuitry 406 maps the received device identifier with the equipment interface unit 106 and with the correct user account at the beginning of the exercise and, during the exercise, the user account manager 406 needs not to receive the device identifier from the equipment interface unit 106 in connection with all the transmissions. Instead, it may use the mapping between the equipment interface unit 106 and the correct user account carried out at the beginning of the exercise through the received device identifier and store the received measurement data into the correct user account by using an identifier of the equipment interface unit received as a source address in connection with all data transmissions transferred over the network connection. In another embodiment, the equipment interface unit 106 transmits the device identifier of the measurement device 102 in all the transmissions transmitted over the network connection, so the user account manager circuitry 406 needs not to make the additional mapping. As a consequence, the user account manager circuitry 406 may directly use the device identifier comprised in the transmission to determine the correct user account to which to store the measurement data. When the server computer 104 receives several types of measurement data, e.g. heart rate data or different types of heart rate data (heart rate, heart rate variability), speed data, etc., the user account manager 402 may classify the received measurement data and store the measurement data into appropriate classes.

In an embodiment, the server computer 104 is configured to carry out real-time computation for the received heart rate measurement data and to return computation results to the equipment interface unit 106 in real-time during the exercise. The computation may be carried out by a heart rate data processor 404. The real-time requirement may be defined as that the server computer 104 processes the heart rate measurement data into advanced performance data as soon as possible, considering the physical restrictions of the server computer, e.g. processing delay and data transfer delay. As a consequence, the server computer 104 may try to avoid adding any intentional delay to the provision of the advanced performance data. Let us now consider the operation of the server computer in this respect with reference to FIG. 5.

Figure 5:
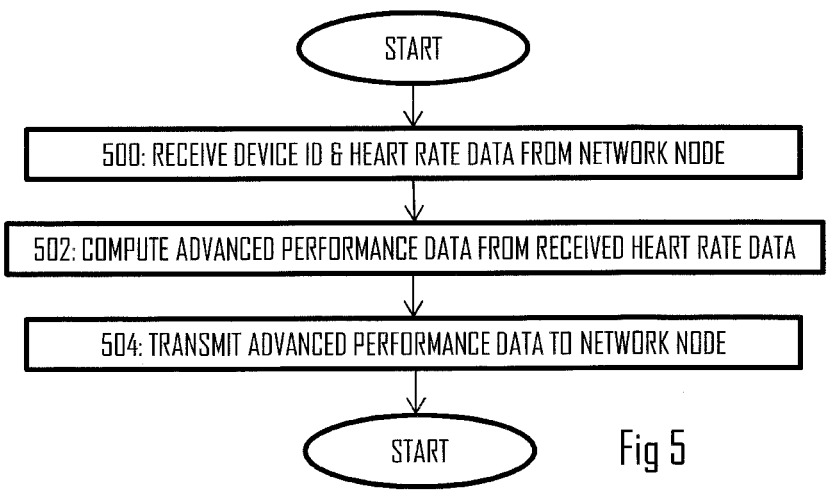
FIG. 5 illustrates a flow diagram of processing received measurement data in the server computer according to an embodiment of the invention.

Referring to FIG. 5, the user account manager circuitry 406 receives the device identifier and the heart rate measurement data from the equipment interface unit 106 in block 500. The user account manager circuitry 406 may store the received heart rate measurement data into the correct user account and, additionally, output the heart rate measurement data to the heart rate data processor 404. In block 502, the heart rate data processor 404 computes the advanced performance data from the received heart rate measurement data.

The advanced performance data may comprise total energy expenditure during the exercise, energy expenditure rates during the exercise, energy expenditure in metabolic component levels, such as fats, carbohydrates and/or proteins. In an embodiment, fitness parameters (e.g. VO2max value known also as maximal oxygen uptake) are calculated by using the heart rate and/or heart rate variability. In this case, the advanced exercise-related data comprises a fitness parameter. The fitness parameter may be presented in any unit, such as activity unit, from which a fitness parameter may be derived. An example of relating activity and fitness parameter is a Jackson formula, which provides a relationship between the maximum oxygen uptake and estimated physical activity. In an embodiment, a relaxation estimate is calculated by using the heart rate variability or a parameter proportional to the heart rate variability. In this case, the advanced performance data may include a relaxation estimate. The relaxation estimate may also be calculated from the power spectrum of an electrocardiography (ECG) derived from the received heart rate measurement data. In an embodiment of the invention, a relaxation estimate may is obtained from the trend of heart rate value when a person is a in a recovery phase after high-load exercise phase. The relaxation estimate may characterize the physical or mental relaxation of a person.

In an embodiment, a training load is calculated on the basis of mechanical stress derived by using the heart rate measurement data and, optionally other measurement data, e.g. motion data and/or pressure information (indicating air/water pressure). The training load characterizes the effect of the training in terms of physical load and the resulting need for recovery. In this case, the advanced performance data may include a training load parameter or an associated recovery need parameter.

In an embodiment, user-specific heart rate zones, such as that based on heart rate variability, are calculated by using the heart rate measurement data.

In an embodiment, a recovery estimate is calculated by using the heart rate measurement data. In this case, the advanced exercise-related data may comprise a recovery estimate. The recovery estimate is a parameter which characterizes the user's recovery status. The recovery estimate may be presented by time required for a desired level of recovery.

In an embodiment, a dehydration estimate is calculated by using the heart rate measurement data. In this case, the advanced performance data may comprise a dehydration estimate. The dehydration estimate may be presented with the amount of beverage or beverage component, such as water or sodium, required to obtain a desired hydration state. In this embodiment, air temperature data measured by a temperature sensor comprised in the measurement device 102 may be used as an additional input to the computation of the dehydration estimate.

Other algorithms known in the field of exercise-related algorithms may be calculated in block 502 as well. Block 502 may also (or alternatively) include comparison of the (processed) measurement data with exercise-guidance parameters stored in the user account as a training program. The current heart rate may be compared with heart rate targets defined for the exercise in the user account. Other measurement data or higher level performance data calculated in block 502 may be compared with corresponding targets stored in the user account so as to determine whether or not the workout follows the predetermined instructions defined in the user account. In these cases, the advanced performance data may comprise indication signals that carry information on the state of the current exercise relative to the predetermined exercise schedule. The indication signal may give rise to audible or visible alarm in the equipment interface unit 106.

In general the advanced performance data the server computer computes repeatedly during the physical exercise and transmits to the equipment interface unit in real time during the physical exercise may comprise at least one value or a metric that accumulates during the physical exercise. Accordingly, the at least one value of the advanced performance data may be a cumulative value. The value may be a numerical value or a verbal value, depending on the each parameter representing the advanced performance data. The parameter value may be a constantly increasing or evolving value that represents the user's performance during the physical exercise. In an embodiment, the advanced performance data informs the user about how much progress the user has made so far, e.g. from the start of the physical exercise to the moment of reception of the latest advanced performance. In another embodiment, the advanced performance data provides an estimate of the future on the basis of the performance made so far, e.g. the recovery estimate.

Computing the advanced performance data in real time repeatedly during the physical exercise from the latest heart rate measurement data allows real time monitoring of the advanced performance data as well. With modern network connections and the processing capability in server computers, the processing and transmission delays may be considered negligible.

In block 504, the heart rate data processor 404 outputs the computer advanced performance data to the network interface 402, and the network interface 402 transmits the advanced performance data to the equipment interface unit 106 over the network connection. The equipment interface unit 106 may then receive the advanced performance data and output the advanced performance data to the user through the user interface of the equipment interface unit 106, for example. The equipment interface unit 106 may, for example, provide display content showing the received advanced performance data simultaneously or alternately with the heart rate measurement data received from the measurement device and/or measurement data measured internally in the equipment interface unit 106. The related processing may comprise determining an identifier of the server computer from which the advanced performance data is received, mapping the identifier with the network address to which the heart rate measurement data was transmitted and, thus, identifying the received advanced performance data as being related to the physical exercise. In another embodiment, the server computer may provide the device identifier of the measurement device 102 together with the advanced performance data, and the equipment interface unit 106 may determine from the received device identifier of the measurement device 102 that the advanced performance data shall be displayed in connection with the heart rate measurement data acquired from the measurement device. Any other identifier enabling the equipment interface unit 106 to associate the received advanced performance data with the current user, user's measurement device, and/or the physical exercise may be used. The equipment interface unit 106 may, instead of or in addition to outputting the advanced performance data to the user, store the advanced performance data in its memory.

The memory 422 of the server computer 104 may further store a computer program code 426 configuring the operation of the processor 420 and, in some embodiments, at least partly the network interface 402. In some embodiments the user account manager circuitry 406 and the heart rate data processor 404 are realized by computer programs carried out by the processor 420. Accordingly, they may be understood as not to form dedicated physical circuitries but to use at least partly the same physical registers, cache memories, and logic units of the processor 420.

Figure 6:
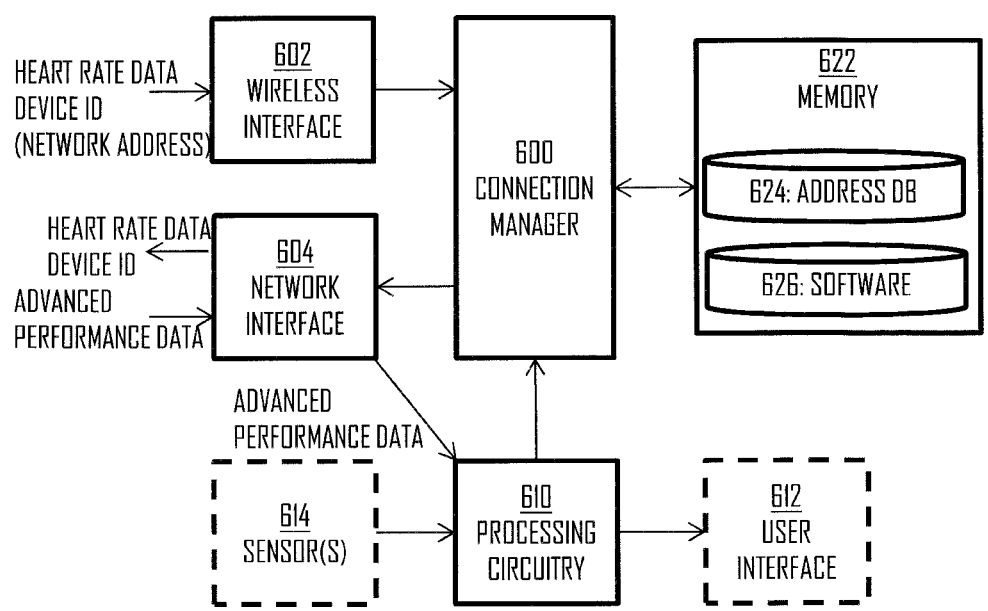
FIG. 6 illustrates a block diagram of an equipment interface unit according to an embodiment of the invention.

FIG. 6 illustrates a block diagram of the equipment interface unit 106 according to an embodiment of the invention. The equipment interface unit may comprise two communication interfaces: one for the device-to-device connection with the measurement device 102 and one for the network connection with the server computer 104. The communication interface used for communicating with the measurement device 102 is called a wireless interface 602. The wireless interface may utilize one of the above-described wireless communication protocols for the device-to-device connection with the measurement device 102 in order to receive the heart rate measurement data, the device identifier of the measurement device 102 and, in some embodiments, the network address of the server computer 104. If the system and the equipment interface unit 106 use the device identifier to derive the network address of the server computer 104, the wireless interface 602 may forward the received device identifier to a connection manager circuitry 600 and, additionally, use the device identifier to identify the measurement device 102 in the device-to-device communication according to the applied wireless communication protocol. The connection manager circuitry 600 may then search an address database 624 storing associations between device identifiers and server computers for the network address associated with the measurement device 102. Upon acquiring the correct network address from the address database 624, the connection manager instructs a network interface 604 forming the other communication interface of the equipment interface unit 106 to establish a network connection with the server computer 104 having the acquired network address. The connection manager circuitry 600 may then map the device-to-device connection between the wireless interface 602 and the measurement device 102 with the network connection between the network interface 604 and the server computer 104.

If the system and the equipment interface unit 106 use the network address provided by the measurement device 102 to derive the network address of the server computer 104, the wireless interface 602 may forward the received device identifier to the connection manager circuitry 600 and use the device identifier only to identify the measurement device 102 in the device-to-device communication according to the applied wireless communication protocol. The connection manager circuitry 600 may then instruct the network interface 604 to establish the network connection with the server computer 104 having the network address received from the measurement device 102. The connection manager circuitry 600 may then map the device-to-device connection between the wireless interface 602 and the measurement device 102 with the network connection between the network interface 604 and the server computer 104.

Upon receiving the heart rate measurement data from the wireless interface 602, the connection manager circuitry 600 may forward the received heart rate measurement data to the network interface 604 or instruct the wireless interface 602 to forward the heart rate measurement data directly to the network interface. If the wireless interface 602 and/or the network interface operates multiple connections simultaneously, the connection manager circuitry 600 may use the mapping to keep the connections of the wireless interface 602 linked with correct network connections operated by the network interface 604.

The wireless interface 602 or the connection manager circuitry 600 may apply the received heart rate measurement data additionally to a processing circuitry 610 configured to process the received heart rate measurement data and compute, for example, the heart rate of the user 100. The heart rate measurement data may comprise heart rate intervals that may or may not be averaged over a few heart rate intervals, e.g. five or less intervals, in the measurement device 102. The processing circuitry 610 may then output the computed heart rate to a user interface 612 for display to the user 100. Similarly, the processing circuitry may process other physiological measurement data received through the wireless interface 602 and/or measured internally in the equipment interface unit 106, e.g. by at least one sensor 614 comprised in the equipment measurement unit. The sensor(s) 614 provided (optionally) in the equipment measurement unit 106 may be fixed or attached to the training device 108, and they may comprise at least one of the following: a grip sensor provided in a grip bar etc. and configured to measure physiological data from user's 100 hand(s) gripping the sensor, a cyclometer or a cadence sensor provided in a training bicycle, etc.

In the embodiments where the equipment interface unit 106 measures the physiological parameters of the user 100 by using the internal sensor(s) 614 in addition to receiving the measurement data from the external measurement device 102, the processing circuitry may apply the internally acquired measurement data to the connection manager circuitry 600, and the connection manager circuitry 600 may configure the network interface 604 to transmit the internal measurement data to the server computer 104 together with the heart rate measurement data received by the wireless interface 602. As a consequence, the connection manager circuitry 600 may map the internal measurement data to the same network connection used for transferring the measurement data acquired from the measurement device 102.

The user interface 612 may comprise a display screen, a loudspeaker, and/or an input device in the form of one or more buttons or switches, keypad etc. In some embodiments, the hardware user interface 612 is omitted.

A memory 622 of the equipment interface unit 106 may store the address database 624 and a computer program code 626 configuring the operation of the connection manager circuitry 600, the processing circuitry 610 and, in some embodiments, at least partly the user interface 612, the network interface 604 and the wireless interface 602.

The equipment interface unit 106 may be provided in the training device 108, or it may be a data router, e.g. a wireless access point. In the latter embodiment, the processing circuitry 610, sensor(s) 614, and the user interface may be omitted from the equipment interface unit 106. The user interface unit may be provided indirectly through computer connected with the data router over a web interface.

As used in this application, the term 'circuitry' refers to all of the following: (a) hardware-only circuit implementations such as implementations in only analog and/or digital circuitry; (b) combinations of circuits and software and/or firmware, such as (as applicable): (i) a combination of processor(s) or processor cores; or (ii) portions of processor(s)/software including digital signal processor(s), software, and at least one memory that work together to cause an apparatus to perform specific functions; and (c) circuits, such as a microprocessor(s) or a portion of a microprocessor(s), that require software or firmware for operation, even if the software or firmware is not physically present.

This definition of 'circuitry' applies to all uses of this term in this application. As a further example, as used in this application, the term "circuitry" would also cover an implementation of merely a processor (or multiple processors) or portion of a processor, e.g. one core of a multi-core processor, and its (or their) accompanying software and/or firmware. The term "circuitry" would also cover, for example and if applicable to the particular element, a baseband integrated circuit, an application-specific integrated circuit (ASIC), and/or a field-programmable grid array (FPGA) circuit for the apparatus according to an embodiment of the invention.

The processes or methods described in FIGS. 2 and 5 may also be carried out in the form of a computer process defined by a computer program. The computer program may be in source code form, object code form, or in some intermediate form, and it may be stored in some sort of carrier, which may be any entity or device capable of carrying the program. Such carriers include transitory and/or non-transitory computer media, e.g. a record medium, computer memory, read-only memory, electrical carrier signal, telecommunications signal, and software distribution package. Depending on the processing power needed, the computer program may be executed in a single electronic digital processing unit or it may be distributed amongst a number of processing units.

Embodiments of the present invention are applicable to training monitoring systems. The protocols used, e.g. the communication protocols, develop constantly and such development may require extra changes to the described embodiments. Therefore, all words and expressions should be interpreted broadly and they are intended to illustrate, not to restrict, the embodiment. It will be obvious to a person skilled in the art that, as technology advances, the inventive concept can be implemented in various ways. The invention and its embodiments are not limited to the examples described above but may vary within the scope of the claims.

What is claimed is:

1. An apparatus comprising:
   a wireless interface configured to provide a wireless device-to-device connection with a measurement device;
   a network interface configured to provide the apparatus with a network connection;
   a user interface;
   at least one processor; and
   at least one memory including a computer program code that, when executed by the at least one processor, causes the apparatus to perform operations comprising:
      receiving, at a beginning of an exercise carried out by a user, a device address from a measurement device attachable to the user's body, wherein the device address comprises a medium access control address or an internet protocol address of the measurement device;
      determining a network address of a server computer to which to route real-time heart rate measurement data acquired from the measurement device during the exercise;
      receiving said heart rate measurement data with the device address from the measurement device through the wireless interface during the exercise;
      causing the network interface to transmit the device address with the heart rate measurement data through the network connection to the network address of the server computer, wherein the server computer uses the device address to identify the measurement device from the received device address, the server computer storing the heart rate measurement data to a user account, the server computer determining the user account based on association of the user account with the device address, the user account being pre-established before the exercise, and wherein the server computer computes, repeatedly during the physical exercise from the heart rate measurement data it receives, advanced performance data comprising at least one value which accumulates during the physical exercise;
      receiving the advanced performance data from the server computer over the network connection during the physical exercise; and
      outputting the advanced performance data to the user.

2. The apparatus of claim 1, wherein the operations further comprise, causing the apparatus to transmit the measurement data to the server computer in real time, as it is being received through the wireless interface.

3. The apparatus of claim 1, wherein the memory is arranged to store an address database linking device addresses of measurement devices with server computer network addresses, and wherein the operations further comprise causing the apparatus to determine the network address of the server computer from the received device address of the measurement device on the basis of said link between the network address of the server computer and the received device address of the measurement device in the database.

4. The apparatus of claim 1, wherein the operations further comprise:
   receiving the network address of the server computer from the measurement device through the wireless interface; and
   determining the network address of the server computer from the network address received from the measurement device.

5. The apparatus of claim 1, further comprising at least one sensor arranged to measure physiological measurement data related to the user during the exercise, and wherein the operations further comprise causing the apparatus to cause the network interface to transmit the physiological measurement data together with the device address of the user's measurement device to the server computer over the same network connection through which the heart rate measurement data is transmitted.

6. The apparatus of claim 1, wherein the advanced performance data is determined based on information stored in the user account before the exercise.

7. The apparatus of claim 6, wherein the advanced performance data comprises a recovery need parameter indicating a need for recovery as a result of the physical exercise and at least one of total energy expenditure during the exercise and energy expenditure in metabolic component levels, the metabolic component levels comprising at least one of fats, carbohydrates, and proteins.

8. The apparatus of claim 1, wherein the at least one value received from the server computer is a numerical value.

* * * * *